United States Patent [19]

O'Connor

[11] 4,250,394
[45] Feb. 10, 1981

[54] APPARATUS FOR DETERMINING IMMUNOCHEMICAL SUBSTANCES

[75] Inventor: John J. O'Connor, Rowland Heights, Calif.

[73] Assignee: Akzona Incorporated, Asheville, N.C.

[21] Appl. No.: 59,098

[22] Filed: Jul. 19, 1979

Related U.S. Application Data

[60] Division of Ser. No. 932,594, Aug. 9, 1978, which is a continuation-in-part of Ser. No. 909,862, May 26, 1978.

[51] Int. Cl.³ .............................................. G01N 15/06
[52] U.S. Cl. .................................. 250/574; 250/576; 356/73; 356/340
[58] Field of Search ............... 250/574, 575, 576, 564, 250/565; 356/440, 442, 340, 73

[56] References Cited

U.S. PATENT DOCUMENTS

| | | | |
|---|---|---|---|
| 3,358,148 | 12/1967 | Conklin et al. | 250/575 |
| 3,573,470 | 4/1971 | Haley | 356/442 X |
| 3,701,620 | 10/1972 | Bergman et al. | 356/340 X |
| 4,195,932 | 4/1980 | Popelka | 356/407 |

OTHER PUBLICATIONS

"Remote Analysis with Lasers and Fibers;" Optical Spectra, May 1980, p. 18.

Primary Examiner—David C. Nelms
Assistant Examiner—Edward P. Westin
Attorney, Agent, or Firm—Robert H. Falk; Charles A. Wendel; Francis W. Young

[57] ABSTRACT

A novel method and a novel apparatus therefor are described for detecting and measuring a predetermined immunochemical substance, for example, an antigen, an antibody, a hapten, or certain low molecular weight substance. The detection and measurement of an immunochemical substance using the method and apparatus of the invention involves providing for the agglutination of a suspension of particles in a sample, or color intensity of solutions by which, using the apparatus of the invention to determine certain electromagnetic radiation properties of the sample, the presence and amount of the immunochemical substance can be determined.

7 Claims, 10 Drawing Figures

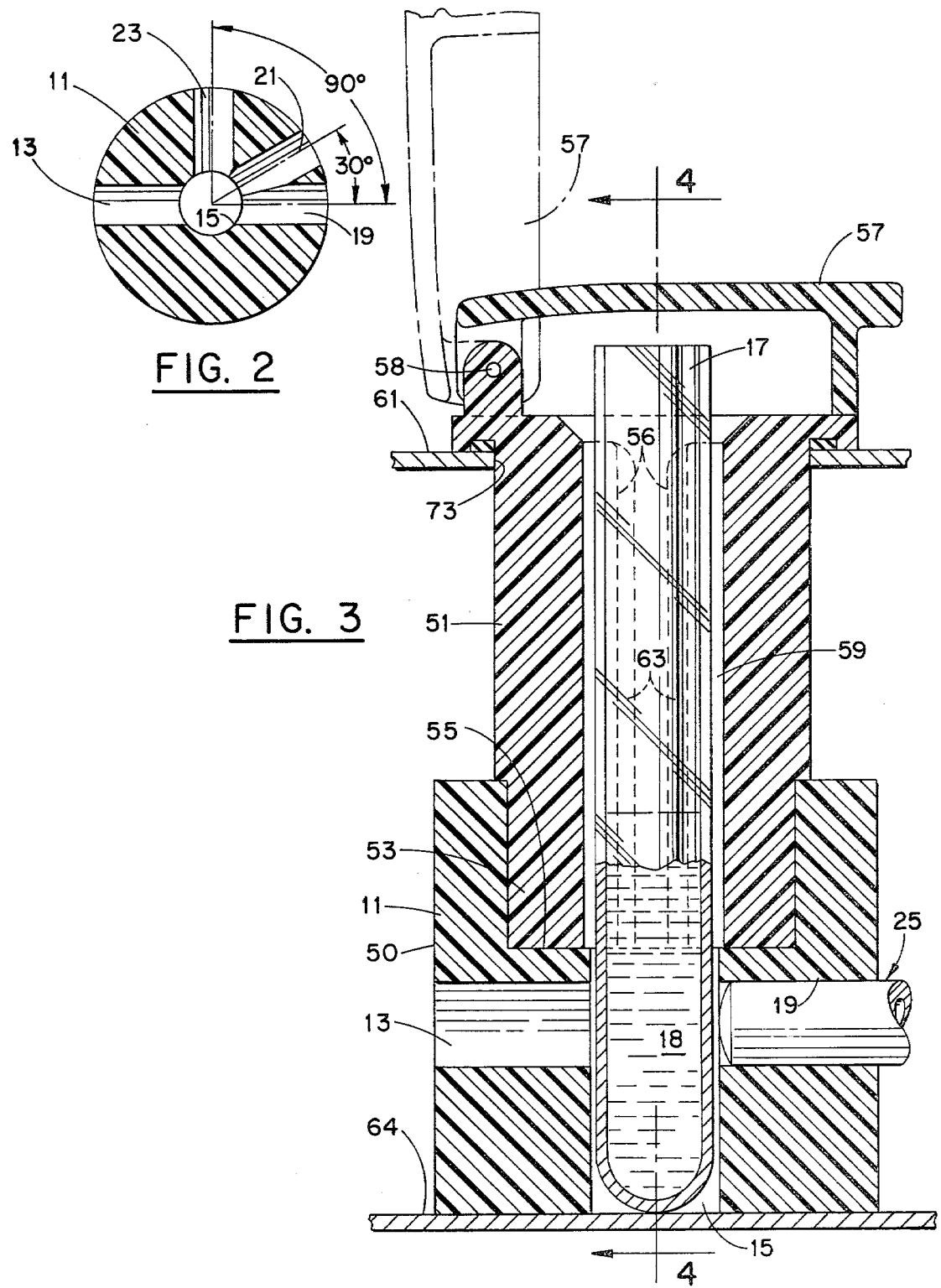

APPARATUS FOR DETERMINING IMMUNOCHEMICAL SUBSTANCES

RELATED APPLICATIONS

This is a division, of application Ser. No. 932,594, filed Aug. 9, 1978, which is a continuation-in-part of Ser. No. 909,862, filed May 26, 1978, of which priority is claimed under 35 USC 120.

BACKGROUND TO THE INVENTION

1. Field of the Invention

The invention relates to the detection and measurement of predetermined immunochemical substances, using a novel method and apparatus therefor which provide for rapid qualitative and quantitative determinations in an advantageous manner.

2. Description of the Prior Art and Other Information

Various methods have been developed in the last two or three decades for the determination of a variety of immunochemical substances, including antigens, antibodies, haptens, and certain low molecular weight substances. Examples of these methods are:

1. Radioassay techniques
   a. Competitive protein binding assays
   b. Radioimmunoassay (RIA)
   c. Immunoradiometric assays
   d. Sandwich or 2-site immunoradiometric assays
2. Fluoroimmunoassays (FIA)
3. Enzyme immunoassay (EIA)
4. Lysis-initiating immunoassays (LIA)
5. Latex-particle agglutination (LPA)
6. Charcoal-particle agglutination (CPA)
7. Hemagglutination and Hemagglutination Inhibition Assays (HA), (HIA)
8. Complement Fixation (CF)
9. Counter-immunoelectrophoresis (CIEP)
10. Radial Immunodiffusion and Double diffusion (RID)
11. Viroimmunoassay (VIA); and
12. Spin immunoassay (SIA) among others.
13. Turbidity (physical assay)

One type of immunochemical test system involves the use of labels. Within these, there are many types of labels useful in assays for the detection and measurement in serum or other media of biologically important or interesting compounds or substances. The administration of most of these tests are hampered by one or more of the following limitations: (1) lack of sensitivity, (2) complexity of the test procedure, (3) instability of reagents, (4) hazardous reagents, (5) impure reagents, and (6) expensive equipment required to perform quantitative and qualitative analysis of the amount of label involved in an immunochemical reaction. For a review of the development and evaluation of immunological methods and their uses as diagnostic tools, reference is made to "Immunology as a Laboratory Tool", by FRANZ PEETOOME, 37 *American Journal of Technology* (2) 445–469 (1971), incorporated herein.

There are other immunochemical test systems which do not use labels for a means of detection; some of these are the so-called "agglutination" tests, wherein the analysis depends on the measurement of certain electromagnetic radiation properties of the liquid samples containing immunochemical constituents, with the measured properties depending on whether or not an immunochemical reaction has taken place. A pioneer reference in this area of technology is Schuurs, U.S. Pat. No. 3,551,555 (1970). See also Price et al, U.S. Pat. No. 4,066,744 (1978); both patents are incorporated herein by reference. Examples of these "agglutination" tests include the so-called "NOSTICON" latex tests by Organon Incorporated (West Orange, New Jersey), including PREGNOSTICON ®, RHEUMANOSTICON ®, and GONOSTICON ® latex agglutination or latex agglutination inhibition Slide Tests (distinguishable from the "NOSTICON" erythrocyte agglutination inhibition tests).

It must be emphasized that both labeled and unlabeled immunochemical testing may employ various devices to separate immunochemical constituents which have reacted from non-reacted immunochemical constituents and from substances irrelevant to the test. For example, some EIA patents require separation through the use of one component in the antigen-antibody reaction being in an "insolubilized" phase for separation-see Schuurs and co-workers in U.S. Pat. Nos. 3,654,090; 3,791,932; 3,850,752; 3,839,153; 3,879,262; 4,016,043 and Reissue 29,169.

Another method does not require separation of free and bound label because the assay depends on the inhibition or activation of the enzyme label by antibody binding (e.g., the EMIT ®-type system of Syva Corporation of Palo Alto, California, for EIA and FRAT, or "free radical assay technique", for SIA)-see U.S. Pat. Nos. 3,880,715; 3,852,157; 3,875,011; 3,935,074; and 3,905,871, and an article by Kenneth S. Rubenstein et al in "Homogenous Enzyme Immunoassay, a New Immunochemical Technique", *Biochemical and Biophysical Research Communications* 47, No. 4, 846–851 (1972) (all incorporated herein by reference). These are examples wherein an insolubilized phase is not employed and the assay depends on inhibition or activation of the enzyme label by antibody binding. See also G. Brian Wisdom, "Enzyme Immunoassay", Clinical Chemistry 22/8, 1243 (1976).

Radioimmunoassay (RIA) is now considered a classical and well-known technique for detecting antigens at very low concentrations. It is based upon the competition between radio-labeled and unlabeled antigen for a fixed, limited amount of antibody, as described by R. Yalow and S. Berson in J. Clin. Invest., 39 1157 (1960). The amount of unlabeled antigen influences the distribution of the labeled antigen in antibody bound (B) and antibody-free (F) labeled antigen, i.e., the more that unlabeled antigen is present, the less the labeled antigen is able to combine with the antibody. In order to obtain conclusive results from the distribution, a good separation between B and F must be made. Methods used for this purpose are, for instance, chromatoelectrophoresis, described by S. Berson and R. Yalow in The Hormones, edited by G. Pincus et al, Academic Press, New York (1964), vol. IV, 557, or insolubilization of the antibodies. This insolubilization can be achieved by chemical means (cross-linking or covalent binding to an insoluble carrier) or by physical methods (adsorption to an insoluble carrier).

Of the limitations cited above, a most serious limitation until recently has been lack of adequate sensitivity to detect some antigens. In general, three levels of sensitivity are recognizable. Low sensitivity techniques, where materials detected and measured exist in microgram/milliliter quantities, include RID, CF, CEP, CPA, and LPA. Intermediate sensitivity techniques, where microgram/milliliter to nanogram/milliliter quantities of materials may be measured, include HIA, HA, CF, FIA, SIA, VIA, and EIA. Until recently only RIA was able to measure with ultrasensitivity the picogram/milliliter to femtogram/milliliter region.

Many of the techniques listed above require that some form of physically or chemically identifiable label be attached to reagents in the assay system in order that the result of a test can be detected. RIA, FIA, EIA, LIA, VIA, and SIA all fall into this category. Radioactivity, fluorescent moieties, enzymes, complement, viruses, and electron-spin labels are used respectively to generate some form of end-point signal. The sensitivity with which these labels can be detected directly and fundamentally affects the useful ranges of the test systems using them.

The sensitivity with which a labeling moiety can be measured depends upon the nature of the signal that it generates, the ability to detect that signal, and the intensity of signal available per unit amount of marker molecule, i.e., its specific activity. With radioactive labels, heretofore the most popular label in use, the signal is decay radiation. Because of the penetrating properties of the emissions generated, radioactive decay can be detected easily. Modern counting equipment very efficiently measures the radioactive emissions from even a small amount of radioactive material. Furthermore, there is a range of specific activities offered by isotopes currently used for tagging.

As noted, up to the present time, the radioimmunoassay (RIA) method in its various forms has been the most sensitive system available. The RIA method, unfortunately, has several serious disadvantages, including the requirement of special equipment, trained staff, the recited need for extra safety measures to protect against harmful radiation, special licensing, controlled radioactive wastes disposal and the continuous disappearance of labeled compound by radioactive decay. The possibility of replacing the radioactive label with an enzyme label was proposed in 1968 in an article by L. E. M. Miles and C. N. Hales, entitled "Labelled Antibodies and Immunological Assay Systems", Lancet, II, 492 (1968), and Nature 219, 168 (1968). No procedural details were provided, the article offered only the general idea, leaving it to future workers to determine the basic step and to perform the extensive experimentation needed to establish a practical operative enzymatic immunoassay method.

More recently, methods for detecting and measuring immunochemical substances have been developed in which, in lieu of a radioactive isotope, immunochemical substances have been labeled with other materials which can be detected by various techniques, e.g., optical and electronic instrument methods. One useful group of materials are enzymes which, because of the great number of analytical permutations, has created a whole family of techniques known collectively as enzyme immunoassay (EIA) techniques.

Among the more recent patents issued that are representative of the state of the art in the detection and measurement of immunochemical substances are, as recited, U.S. Pat. Nos. 3,654,090, issued Apr. 4, 1972; 3,666,421, issued May 30, 1972; 3,791,932, issued Feb. 12, 1974; 3,839,153, issued Oct. 1, 1974; 3,850,752, issued Nov. 26, 1974; 3,879,262, issued Apr. 22, 1975; 4,016,043, issued Apr. 5, 1977; and Reissue Pat. No. 29,169, reissued Apr. 5, 1977, all incorporated by reference herein.

A specific example of a recent latex agglutination inhibition method is a qualitative in vitro test for determining the presence of human chorionic gonadotropin (HCG). HCG is a hormone that is characteristic of pregnancy and may be found in the urine of a pregnant human. An antiserum specific to HCG can be prepared from rabbits immunized with HCG to produce the antibody.

According to the PREGNOSTICON ® Slide Test, if the antiserum is mixed with latex that has been sensitized with HCG, agglutination of the latex occurs. If, on the other hand, the antiserum is mixed with a sample of urine containing HCG, i.e., from a pregnant person, the antiserum is neutralized, and upon subsequent mixing of the antiserum-urine mixture with the HCG-sensitized latex, the agglutination of the latex is inhibited. The latex appears as a milky homogenous suspension, its agglutination having been inhibited. This is a positive test for pregnancy.

Although usually a positive or negative result can be determined by of lack of agglutination or agglutination of the latex, respectively, a maximum inhibition of agglutination may not occur in the early stages of pregnancy when the concentration of HCG in the urine has not increased above a certain threshold level which can be detected by this method. The sensitivity of the described pregnancy test is normally such that the concentration levels of HCG are usually sufficiently elevated by the twelfth day after menstruation fails to occur that the HCG can be detected with the test. If the result of the test is inconclusive, the test must be conducted again in another week or two, to allow sufficient time for an increase in the HCG concentration in the urine to detectable levels. Of course, this is very undesirable from a diagnostic viewpoint, since it is often important to be able to determine the existence of pregnancy at the earliest stages.

The above-described test is qualitative in nature, giving either a positive or a negative test for some threshold concentration of HCG. If HCG is detected in a urine sample, a more quantitative determination of the concentration of HCG in the sample can be made by conducting a series of tests on a series of systematic serial dilutions (commonly referred to in the art as a "dilution series") of the urine samples. Of course, the necessity of conducting a series of tests to determine the concentration of HCG in a single urine sample is time-consuming and costly.

In an available embodiment, the foregoing technique for qualitatively detecting the HCG antigen characteristic of pregnancy is known as the PREGNOSTICON ®-Slide Test (Organon Inc., West Orange, New Jersey).

The same general agglutination process principles underlying the PREGNOSTICON ®-Slide Test (and erythrocyte test) can also be applied to the determination of other immunochemical substances which can be specifically bound, such as antigens i.e., those associated with gonorrhea, rheumatoid factor, etc., and antibodies such as those specific to GC, IgG, and so forth. It would be desirable to provide to provide a test for determining immunochemical substances which would both detect and quantitatively measure the presence of such specifically-bindable immunochemical substances rapidly and at low concentrations, to thereby insure early diagnosis.

The use of light-scattering photometers in analyzing the electromagnetic properties of various substances is well known and photometric methods can be used in the analysis of immunochemical substances. There are many different embodiments in which light-scattering photometers have been used, but most cases, such instrumentation is very sophisticated and expensive. One reason for this is that such instruments typically include a number of lens systems and complicated mechanisms for positioning the cuvette containing the substance being determined, for example, the BRICE-PHOENIX Model OM-2000 Light Scattering Photometer (Virtis Co., Gardiner, New York); SCIENCE SPECTRUM Differential Light-Scattering ® Photometer (Santa Barbara, Cal.). For example, U.S. Pat. No. 3,036,492 issued May 29, 1962, describes a complex adjustable specimen chamber for determining the light transmittance properties of a sample at varying angles. Another example is U.S. Pat. No. 3,918,817 issued Nov. 11, 1975, which describes a turbidimeter, a particular type of photometer, including a special thermal insulating housing and using a glass test tube of rectangular cross-section. Buffone, "Improved Nephelometric Instrumentation", *Laboratory Management*, April, 1977, describes at page 19 a nephelometer, a similar type of photometer, using an incandescent lamp with filters to produce a band of radiation between 450 and 650 mn.

In general, much of the existing literature has been concerned primarily with textile quality control techniques. For example, in other variations involving the use of light-scattering photometers, textile color analyzers involving instrument heads using a plurality of fiber-optic bundles positioned to receive diffuse light reflected from the textile samples have been devised, as described in U.S. Pat. No. 3,986,778 issued Oct. 19, 1976, and U.S. Pat. No. 3,999,860 issued Dec. 28, 1976.

It is interesting to note that light-scattering photometric methods for determining particular substances have in the past typically required measurement at a particular wavelength, that is, essentially monochromatic light.

For instance, in Blume and Greenberg, "Application of Differential Light Scattering to the Latex Agglutination Assay for Rheumatoid Factor" Clinical Chemistry, Vol. 21, No. 9, 1975, page 1234 et seq., it is disclosed that in the technique of differential light scattering it is essential that the light source be highly monochromatic, such as, e.g., that produced by a helium/neon-laser (632.8 nm). The requirement of essentially monochromatic light in photometric determinations is again described by Lichenbelt, Pallmarnanobaran, and Wiersema, "Rapid Coagulation of Polystyrene Latex in a Stopped Flow Spectrophotometer", *Journal of Colloid & Interface Science*, Vol. 49, No. 2, 1974, page 281 et seq., and Dininno and McCandless, "Agarose Medium Turbidimetric Assay for Cross-Reacting Antigens", *Journal of Immunological Methods*, Vol. 17, 1977, pages 73-79. See also *Flurometry Reviews*, March 1969 (monthly bulletin of Turner Inc., Palo Alto, California).

Surprisingly, it has now been found in the instant invention that for the detection and measurement of insolubilized particles in suspension, i.e., non-agglutinated or agglutinated latex particles, turbid liquid samples, chemical precipitates, etc., the requirement for a monochromatic, incident light source is illusory. It has also been found in the instant invention that the widest spectral band of incident light available, whose upper wavelength limit being equal to or less than the mean diameter of the insolubilized particles in the suspension of interest (the value herein which may be expressed in nanometers or microns), is preferred for optimum detection and measurement sensitivity. The use of such wide-band spectral filters, commonly known as low-pass optical filters, in association with an appropriate light source, is indeed unique and novel for the aforementioned applications.

The use of such low-pass optical filters are suitable for forward-scattering measurements at the 0° optical-axis mode as well as for light-scattering measurements at any off-axis detection angle mode from 1° to 90° to the optical axis of the text system. The 90° detection mode is more commonly known as the nephelometric mode. Examples of present art for the 0° detection mode is the Klett-Summerson Model 900-3 colorimeter (Klett Mfg. Co.); for off-axis detection modes, the Brice-Phoenix Models 2000D and 2000DM Light-Scattering Photometers (Phoenix Precision Instrument Company); and for the 90° detection mode, the Volu-Sol Models 300 and 299 Nephelometers (Volu-Sol Medical Ind., Inc.).

The preceding discussion illustrates that a need exists for (a) new improved methods and (b) low cost, simple to use apparatus therefor for making rapid, accurate, and economical measurements of immunochemical substances in agglutination and colorimetric medical-diagnostic laboratory tests employing inexpensive disposable cuvettes (having scratches and small defects) normally manufactured for the science laboratory.

SUMMARY OF THE INVENTION

The invention relates to the detection and measurement of predetermined, specifically-bindable, immunochemical substances in agglutination-type immunochemical test systems or labeled immunochemical systems (as are known to those skilled in the art, such as EIA or FIA, subject to spectrophotometric, colorimetric, or nephelometric analysis, using a novel method and novel apparatus therefor that provide for rapid and accurate quantitative determinations in an efficient and economical manner. It must also be understood that the invention relates to the detection and measurement of particles by turbidimetry, and to the demonstration and determination, i.e., qualitative and quantitative analysis, of clarity of various non-opaque liquids, whether or not containing suspensions of particles therein.

The devices, i.e., novel features of the invention, may have direct applications in other analytical instrumentation for studying molecular and micellar weights of compounds (from about $3 \times 10^2$ to about $10^9$), particle size and size distributions shapes and orientations of macromolecules, interactions in solutions, kinetics of reactions, and polarization of fluoresence, as well as the optical properties of liquids by measuring (as the case might be) turbidity, forward light scattering, off-axis light scattering, transmitted light, optical density, depolarization or fluorescence. As will be appreciated by those in the art, it must be understood that qualitative analysis is inclusive in the phrase "detection and measurement" or the equivalent, and that the user, of course, need not at his option utilize the data provided by the method for a quantitative analysis; i.e., "detection and measurement" may be read "detection and measurement, or, if desired, only detection."

In a preferred embodiment of the invention there is provided an optical method for detecting and measuring in a liquid sample, comprising a suspension of coated (preferably latex) particles, the presence and concentration of a predetermined immunochemical substance in the sample. By measuring the electromagnetic radiation transmission properties of the sample using a calibrated radiation-measuring apparatus according to the novel apparatus of the invention, the presence and concentration of the immunochemical substance can be determined.

The novel method for detection and measuring a predetermined specifically-bindable immunochemical substance in a liquid sample, comprises the steps of:

(a) providing, in an immunoassay technique for a liquid sample, a component comprising a suspension of particles which may be agglutinated or insolubilized in relationship to the presence and concentration of the immunochemical substance in the sample; and (b) determining the presence and concentration of the immunochemical substance by measuring the electromagnetic radiation transmission properties of the sample using a calibrated radiation-measuring apparatus, said apparatus comprising:

(1) a suitable electromagnetic radiation source capable of providing radiation at wavelengths equal to or less than the mean diameter of said particles;

(2) means for concentrating and collimating radiation from the electromagnetic radiation source to form a beam;

(3) means for filtering the beam to (i) eliminate radiation having wavelengths greater than the mean diameter of the particles and (ii) transmit radiation of a wavelength equal to or below the mean diameter of the particles over a wavelength range of at least 100 nm;

(4) means for (i) positioning a sample-containing cuvette and for (ii) allowing the filtered beam incident on the cuvette to be transmitted through the cuvette and sample, and for (iii) receiving a portion of the filtered beam transmitted through the sample at two or more predetermined angles with respect to the beam; and (5) means for detecting and measuring the portion of the beam transmitted at a predetermined angle.

The novel apparatus of the invention for detecting and measuring electromagnetic radiation transmitted at predetermined angles through a liquid sample having a suspension of particles comprises:

(a) a suitable electromagnetic radiation source capable of providing radiation at wavelengths equal to or less than the mean diameter of the particles;

(b) means for concentrating and collimating radiation from said electromagnetic radiation source to form a beam;

(c) means for filtering the beam to (i) eliminate radiation having wavelengths greater than the mean diameter of the particles and (ii) transmit radiation of a wavelength below the mean diameter of the particles over a wavelength range of at least 100 nm;

(d) means for (i) positioning a sample-containing cuvette and for (ii) allowing the filtered beam incident on the cuvette to be transmitted through the cuvette and sample, and for (iii) receiving a portion of the filtered beam transmitted through the sample at two or more predetermined angles with respect to the beam, comprising:

a cuvette fixture comprising a tubular incident radiation beam aperture, tubular cuvette opening, and at least two tubular radiation-receiving apertures, wherein the axes of all the apertures are coplanar and intersect along the axis of the cuvette opening and are perpendicular to the cuvette opening, and wherein the axes of the radiation-receiving apertures are fixed at predetermined angles with respect to the axes of (1) the incident radiation beam aperture and (2) the tubular cuvette opening, and attached thereto; and a receptor-conveyor means comprising a tubular fiber-optic bundle terminated at one end by a substantially coaxial tubular detector cone, wherein the detector cone is (1) inserted in sealing engagement with one of said radiation-beam receiving apertures, (2) has a substantially coaxial orifice at the end of the detector cone remote from the bundle at a distance such that electromagnetic radiation is transmitted at about a 6° admittance angle from the orifice to said fiber-optic bundle, the orifice being at the intersection of the receiving aperture and the cuvette opening; and (e) means with the non-cone-terminated end of the fiber-optic bundle and with the cuvette-positioning means for detecting and measuring substantially only a portion of the transmitted beam. Preferably, the means with the non-terminated end of the fiber-optic bundle comprises a signal processing circuit with a photodiode.

The mean diameter of the particles may generally be from about 0.20 μm to about 1.3 μm, preferably from 0.40 μm to about 0.65 μm, and most preferably about 0.45 μm, so long as the light source provides radiation of a wavelength below said mean diameter over a wavelength range of at least about 100 nm.

The apparatus of the invention can be operated at ambient conditions of temperature, pressure and humidity in an ordinary light-filled room, and has the advantage of no moving parts and mechanical adjustments that encumbered the prior art.

BRIEF DESCRIPTION OF THE DRAWINGS

FIG. 2 shows an enlarged and more detailed view of the cuvette fixture depicted in the schematic diagram of FIG. 1.

FIG. 3 shows a vertical sectional view of the cuvette fixture of the apparatus.

PREFERRED TYPES OF IMMUNOCHEMICAL TESTS

Figure 1:
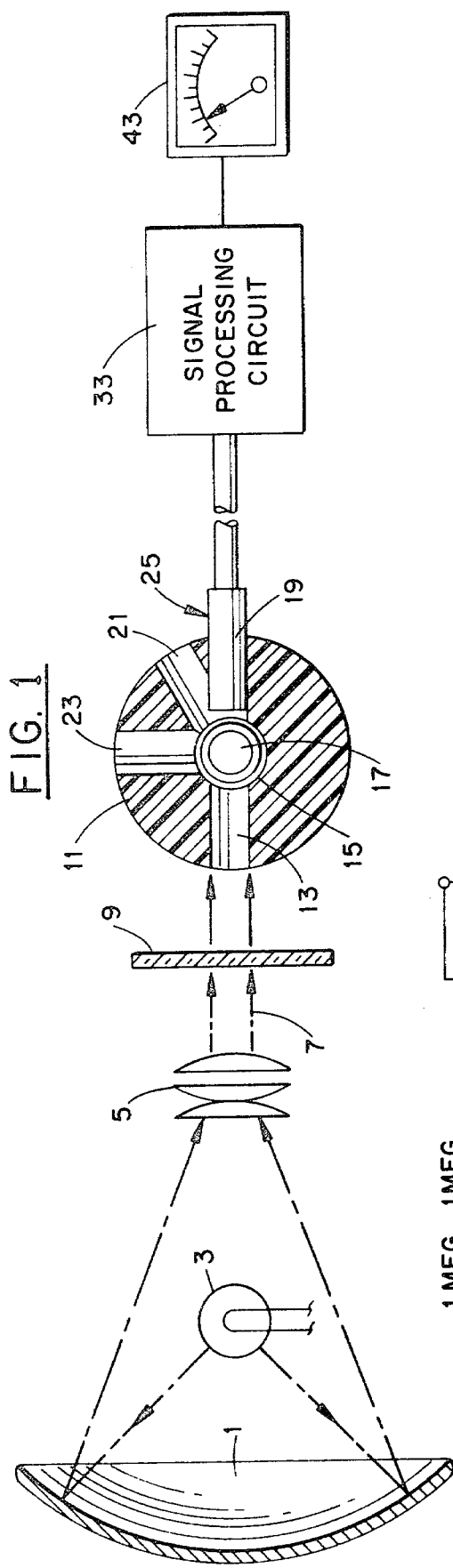
FIG. 1 represents an overall schematic diagram of an apparatus according to the invention.

While applicable to any labeled system subject to photometric analysis for detection and measurement of the immunochemical substance to be determined, the instant invention is preferably applied to any of the insolubilized agglutination and EIA tests commercially available. The latex agglutination tests may be utilized in the methods of Schuurs in U.S. Pat. No. 3,551,555 (1970) and Price et al, U.S. Pat. No. 4,066,744 (1978). The aforementioned EIA diagnostics tests are represented by Schuurs U.S. Pat. No. 3,654,090 and its progeny as mentioned above.

Enzyme-marked compounds for use in enzyme-immunoassays (EIA) now possess, for most antigens and antibodies to be detected, all of the advantageous properties that were formerly achieved only by radioimmunoassay (RIA): e.g., high specific activity (enzymatic or radioactive), chemical stability, immunologic similarity to the substance to be measured, and chemical purity.

If an EIA technique is employed, the choice of the enzyme which is taken up in the coupling product is determined by a number of properties of that enzyme. It is, of course, essential that the catalytic property of the enzyme should be resistant to the coupling with another molecule. Also of great importance is the specific activity of the enzyme. As less enzyme conjugate is needed to be added to reach a measurable enzyme effect, the sensitivity of an immunoassay system can be increased. With a specified enzyme whose rate of conversion is fixed and whose purity is high, the specific activity of a labeled compound is proportional to the degree of incorporation of enzyme molecules per molecule of marked substance, and a higher specific enzymatic activity results. See German Pat. No. 2,430,356 (1975); German Pat. No. 2,557,419 (1976); U.S. Pat. No. 3,853,987 (1974); Michel F. Aubert, "Critical Study of the Radioimmunological Assay for the Dosage of the Polypeptide Hormones in Plasma", *J. Nuclear and Biological Medicine* 13, 1–19 (1970); Robert Roberts and A. Painter, "Radioimmunoassay for Carrier Creatine Kinase Isoenzymes", 480 *Biochimica Biophysica Aeta* 521–526 (1977); Michael G. Grattain, J. M. Puttman, and T. G. Pretlow in "The Use of Glutaraldehyde-Conjugated Horseradish Peroxidase-Bovine Serum Albumin in the Visualization of Concanavalin A Binding to Tissue Sections of Human Colonic Tumor", *Laboratory Investigation* 35/6, 537–541 (1976), incorporated herein by reference.

Those enzymes can be determined colorimetrically that catalyze a reaction in which a colored substance appears or disappears.

Also, the enzyme should be stable when stored for a period of at least three months, and preferably at least six months at temperatures which are convenient for storage in the laboratory, normally about 4° C. or below.

A product should be either formed or destroyed as a result of the enzyme reaction, which product absorbs light in the ultra-violet region or the visible region, that is in the range of about 250–750 nm, preferably 300–600 nm.

The enzyme should have a satisfactory turnover rate at or near the pH optimum for immunoassay conditions; this is normally at about pH 6–10, and most typically from about 6.0 to about 8.0. Preferably, the enzyme will have the pH optimum for the turnover rate at or near the pH optimum for binding of the antibody to the liquid.

The enzyme which is employed or other enzymes with like activity will not be present in the fluid to be measured, or can be easily removed or deactivated prior to the addition of the assay reagents. Also, one must insure that naturally occurring inhibitors for the enzyme present in fluids to be assayed are not present in concentrations at which they will interfere.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

A summary of properties of enzymes useful for enzyme labels is given below:

1. Available and inexpensive in high purity.
2. High enzymatic specific activity.
3. Soluble under labeling and assay conditions.
4. Chemically and functionally stable under labeling and assay conditions.
5. Enzymatic activity detected simply, sensitively, inexpensively, rapidly and with standard laboratory equipment.
6. Missing or in negligible concentration in analyte.
7. Interfering factors missing in analysis.

Enzymes currently used as labeling moieties in enzyme immunoassay (from G. B. Wisdom, *Clinical Chemistry* 22, No. 6, 1243–1255 (1976)) are shown in Table I.

TABLE I

| Enzymes Currently Used as Labeling Moieties in Enzyme Immunoassay | | |
|---|---|---|
| Enzyme | Source | Enzyme Commission |
| Malate dehydrogenase | Pig heart mitochondria | 1.1.1.37 |
| Glucose-6-phosphate dehydrogenase | *Leuconostoc mesenteroides* | 1.1.1.49 |
| Glucose oxidase | Fungal | 1.1.3.4 |
| Peroxidase | Horse-radish | 1.11.1.7 |
| Acetylcholinesterase | Bovine erythrocytes | 3.1.1.7 |
| Alkaline phosphatase | Calf intestinal mucosa and *E. coli* | 3.1.3.1 |
| Glucoamylase | *Rhizopus nivens* | 3.2.1.3 |
| Lysozyme | Egg white | 3.2.1.17 |
| β-Galactosidase | *E. coli* | 3.2.1.23 |

Preferable enzymes generally include catalase, peroxidases, β-qlucosidase, β-D-galactosidase, β-D-glucosidase, urease, qlucose oxidase, qalactose oxidase, and alkaline phosphatase; in general the qlucuronidases, qalactosidases, ureases and the oxidoreductases. An extremely preferable enzyme is horseradish peroxidase (HRP) which can be obtained relatively inexpensively for pure material, has a high conversion of substrate, and has a substantially flat, fixed rate of conversion.

Use of an enzyme immunoassay system offers attractive advantages: elimination of radioactive substances and their associated hazards and license requirements, common, inexpensive laboratory equipment used, amplification of results through repeated use of enzyme catalysis (a radio-isotope atom decays only once) and ready availability commercially of the enzymes. Unlike radioactively labeled compounds where high specific radioactivities lead to increased auto-radiolytic destruction, these high specific enzymatic activity enzyme systems are stable chemically, there being no radioactive emissions present to cause destruction. Hence, preferable markers for the invention are suitable enzymes, with HRP being most preferable.

As known to those skilled in the art, in some instances a "cofactor" of coenzyme, which is a small nonprotein prosthetic group (i.e., compound), is required before an enzyme can exert its catalytic effect on a substrate. An example of such an enzyme is malate dehydrogenase.

The novel method and novel apparatus are also especially suited for agglutination-type immunochemical tests i.e., the so-called latex agglutination tests such as the "NOSTICON" tests mentioned above.

The term "antibody" or "antibodies" as employed herein means a group of serum proteins, also referred to as gamma globulins or immunoglobulins, that will specifically react with an antigen. Most of these antibodies belong to the IgG class, while the other classes are termed IgA, IgM, IgD, and IgE. It is also used herein to include certain naturally occurring binding proteins which recognize certain humoral constituents, for example, such proteins for testosterone, cortisol and thyroxine.

The term "antigen" is employed herein to mean a substance that will react with an antibody. Antigens are often characterized as capable of inducing the formation of an antibody and of reacting with that antibody. However, as will be recognized by those in the art, in the case of "haptens", defined infra, it is necessary to be coupled to a carrier such as, for example, inert adsorbing particles, synthetic peptides, or natural protein molecules, in order to induce antibody formation. Materials commonly employed as carriers include, for example, the albumins (human, bovine, or rabbit), synthetic polypeptides (for example, polylysine), inert adsorbing particles (for example, charcoal particles) and polymers (for example, dextrans). It is noted that haptens will, in the absence of a carrier, still react with antibodies and can be employed in the antigen-antibody reaction assays of the present invention either with or without carriers.

The term "pure protein" or simply "protein" as employed herein is intended to include proteins and polypeptides that are free of contamination, and it is good practice to use such pure material to avoid unnecessary interfering factors.

The following Table II lists a partial representation of diseases, causative organisms, antigens, and antibodies within the scope of the invention:

TABLE II

REPRESENTATIVE ANTIGENS AND ANTIBODIES
Disease States and Antigen Derived From the Causative Organism or Other Specific Antigens Used in the Diagnosis of Certain Disease States I. Infectious Diseases.

| Disease | Organism | Antigen |
|---|---|---|
| A. Parasites | | |
| Amoebiasis | Entamoeba histolytica | Organism sonicate of strain HK-9 |
| Toxoplasmosis | Toxoplasma gondii | Whole organism or their sonicate derived from tissue culture or mouse peritoneal fluid |
| Chaqas | Trypanosoma cruzi | Organism sonicate derived from tissue culture |
| Schistosomiasis | Schistosoma haematobium Schistosoma japonicum Schistosoma mansoni | Culture filtrates |
| B. Bacteria | | |
| Infectious meningitis | Neisseria meningitidis | Capsular polysaccharide |
| Gonorrhea | Neisseria gonorrhoeae | Pili isolated from the bacterial cells |
| Typhoid fever | Salmonella typhi | Bacterial cells or their extracts |
| Pneumonia | Diolococcus pneumoniae | Capsular polysaccharide |

TABLE II-continued

REPRESENTATIVE ANTIGENS AND ANTIBODIES
Disease States and Antigen Derived From the Causative Organism or Other Specific Antigens Used in the Diagnosis of Certain Disease States I. Infectious Diseases.

| Disease | Organism | Antigen |
|---|---|---|
| C. Fungi | | |
| Histoplasmosis | Histoplasma capsulatum | Culture filtrate |
| Blastomycosis | Blastomyces dermatitidis | Culture filtrate |
| Coccidioidomycosis | Coccidioides immitis | Culture filtrate |
| D. Viruses | | |
| Rubella | Rubella virus | Virus particles |
| Measles (Rubeola) | Measles virus | Virus particles |
| Rabies | Rabies virus | Virus particles |
| E. Allergies | | |
| | Ragweed pollen | Pollen extract |
| | Tomatoes | Tomato extract |
| | Bermuda grass seed | Seed extract |
| | Cat dander | Fur extract |
| | House dirt | Dust extract |
| F. Disease States | | |
| Lupus Erythematosis | | DNA molecules RNA molecules |
| Rheumatoid arthritis | | Human IgG |
| Colon cancer | | CEA antigen |
| Hepatoma | | Alpha-1-feto protein |

The novel apparatus and method of the invention can also be employed for the determination of haptens, which may be regarded as a special group of low molecular compounds, and their anti-substances. These substances mostly occur in low concentrations. As will be recognized by those in the art, and according to the original definition of K. Landsteiner, haptens are protein-free substances whose chemical configuration is such that they can react with specific antibodies, but not such that they are capable of causing the formation of antibodies. In order to be able yet to make antibodies against haptens, the haptens must be coupled to polypeptides, inert adsorbing particles, or natural protein molecules before being injected into a test animal. In the determination of a low molecular weight compound by classical enzyme immunoassay (EIA), the substance to be determined and its enzyme conjugate enter into competition for a given quantity of the antibody. The more unlabeled compound the sample contains, the less the soluble enzyme conjugate of that compound is able to combine with the specific binding protein and the more of the conjugate will remain unbound in the liquid phase. Following a separation of bound and free phases (frequently but not always necessary), the enzyme activity can be measured in a simple manner.

As examples of haptens are mentioned: steroids, such as estrone, estradiol, estriol, cortisol, cortisone, testosterone, pregnanediol, and progesterone; vitamins, such as vitamin $B_{12}$ and folic acid; 1-thyroxine; triiodo-1-thyronine; histamine; serotonin; digoxin; prostaglandin; adrenalin; noradrenalin; morphine; vegetable hormones such as auxin, kinetin and gibberellic acid; and antibiotics, such as penicillin.

Hence, the compound or substance to be labeled is a conventional diagnostic material such as a hapten, a drug, a hormone, a protein, nucleic acid or other biologically or immunologically useful or interesting molecule, or viruses or bacteria. If an enzyme marker is chosen and a preference is made to use an insolubilized phase in the reaction scheme, one may adapt the novel process and method for a simple "competitive" method (as taught in U.S. Pat. No. 3,654,090), or for a "sandwich" method (as taught in U.S. Pat. No. 4,016,043 or U.S. Reissue Pat. No. 29,169, for example), or for a double antibody solid phase "DASP" method (as taught in U.S. Pat. No. 3,839,153). The instantly claimed method and apparatus of the invention can be used with conventional test kits, for example, those kits also set forth in detail in U.S. Pat. Nos. 3,654,090; 3,850,752; 3,838,153; 3,879,262; and 4,016,043. The term "kit" is employed herein to mean a collection of all or some of the chemicals, including the assay tubes or cuvettes, and instructions necessary to do a enzyme immunoassay.

DESCRIPTION OF PREFERRED EMBODIMENTS

The practice of the novel method of the invention involves in each case the determination of the electromagnetic radiation transmission properties of a sample in a cuvette using the novel apparatus of the invention.

The apparatus is most conveniently discussed by reference to the drawings, although it is to be understood that the drawings are referred to only for purposes of illustration and example, and the scope of the invention is not limited thereto.

In FIG. 1, the apparatus of the invention is shown schematically. As depicted, mirror 1 (Rolyn 61.200) and lens assembly 5 act to concentrate and collimate the electromagnetic radiation emitted by electromagnetic radiation source 3 (here a Sylvania 6.6A/T2.5Q/Cl quartz-halogen lamp) to form a beam 7. The lens assembly 5 usually comprises two condenser lens (Rolyn 10.0140) and a collimator lens (Rolyn 10.0050). It is preferable to surround the beam 7 by a black barrel (not shown) slightly greater than the diameter of the incident radiation beam aperture 13 so as not to lose appreciable energy. A low-pass optical filter 9 is interposed in the path of the beam to modify certain characteristics of the beam, as discussed hereinafter, before the beam reaches cuvette fixture 11 at tubular incident radiation beam aperture 13. Preferably, a standard Leitz-Wetzlar BG12 filter is employed.

A cuvette fixture 11 provides a means for positioning a sample-containing cuvette 17 and allowing the filtered beam incident to the cuvette to be transmitted through the cuvette and sample. The cuvette fixture is preferably machined from a DELRIN ® (du Pont) black resin material (machined by Organon). A receptor-conveyor means 25 is snugly positioned in one of alternate radiation receiving apertures 19, 21 and 23 originating through cuvette opening 15 and providing a means for receiving a portion of the filtered beam transmitted through the sample at a predetermined angle with respect to the axis of incident radiation beam aperture 13.

A suitable light transmission means such as a fiber optic bundle 27 (here a Skia bundle, LG-093-008, not shown in FIG. 1) comprising a part of a receptor-conveyor means 25 (or receptor-assembly) conveys the received radiation from cuvette fixture 11 to signal processing circuit 33, which transforms the signal received into a needle displacement in meter 43, indicative of the electromagnetic radiation transmission properties of the sample.

The electromagnetic radiation source 3 suitable according to the invention must be capable of providing radiation at relatively short wavelengths, i.e., providing electromagnetic radiation of at least 100 nm width and having an upper bounds slightly more than the mean diameter of the particles used in the method of the invention. In a preferred embodiment the electromagnetic radiation source is a quartz-halogen lamp.

The radiation from electromagnetic radiation source 3 is concentrated and collimated to form a beam 7 by means of mirror 1 and lenses 5. The representation of the mirror 1 and the lens 5 in FIG. 1 is schematic only, it being understood that those skilled in the art could devise a variety of different mirror and lens configurations to thereby concentrate and collimate the radiation to form a beam.

Filter 9 modifies the beam by eliminating radiation having wavelengths greater than the mean diameter of the particles (generally about 0.45 μm for latex particles) and, as recited, by transmitting radiation below the mean diameter over a wavelength range of at least 100 nm, e.g., 300 to 450 nm for latex particles. As is known to those skilled in the art, glass (other than quartz) absorbs most electromagnetic radiation having a wavelength below about 300 nm, although if this radiation energy were available, one would desire not to eliminate this radiation. In a preferred embodiment the filter is a so-called low-pass optical filter, i.e., a filter which is so selected and manufactured to transmit essentially all radiation below a characteristic wavelength (here the mean diameter of the particles) down to very short wavelengths at which the matrix material comprising the filter exhibits absorption. Of course, as one in the art can appreciate, one can adjust to a given mean diameter for a set of particles in suspension by changing the filter, and if necessary, the light radiation source.

The cuvette fixture 11 shown schematically in FIG. 1 is more particularly described by reference to FIGS. 2, 3, 4 and 5. In FIG. 2, cuvette fixture 11 provides a means for positioning a cuvette 17 (not shown—see FIG. 3) containing a liquid sample 18 (not shown—see FIG. 3) prepared according to the method of the invention to allow the filtered beam to be transmitted through the cuvette and sample.

The cuvette fixture comprises a tubular incident radiation beam aperture and at least two tubular radiation-receiving apertures. As noted above, and as shown in FIGS. 1–5, cuvette fixture 11 comprises tubular incident radiation beam aperture 13 and tubular radiation-receiving apertures 19, 21 and 23. The incident radiation beam aperture and the radiation-receiving beam apertures are coplanar, and intersect along the axis of cuvette opening 15, to which they are perpendicular.

Furthermore, in addition to being perpendicular to the axis of cuvette opening 15, the axes of the radiation-receiving apertures are also fixed at predetermined angles with respect to the axis of the incident radiation beam aperture 13. In the preferred embodiment shown in FIG. 2, the predetermined angles of radiation-receiving apertures 19, 21 and 23 have arbitrarily been chosen to be 0° (parallel), 30° and 90°, respectively. One skilled in the art could locate apertures at different angles if desired. For the latex agglutination tests, it is recommended that the 0° (or colorimetric) position be used; for the detection of globulins, the 30° light scattering position is recommended; finally, for the detection of precipitates and turbidity, the 90° nephelometric position is recommended.

Returning to FIG. 3, in the method of the invention the cuvette 17, containing the sample 18, is positioned within the tubular cuvette opening 15 so as to occupy the space between the incident radiation beam aperture 13 and the tubular radiation-receiving apertures.

Cuvettes for various samples should be reproducibly positioned within the tubular cuvette opening to insure uniformity in the distance of the radiation transmission through the sample and cuvette. Reproducible positioning of the cuvette can be accomplished by a variety of binding techniques, such as, for example, that shown in FIGS. 3, 4 and 5.

Cuvette-holder assembly 11 is comprised of two principle parts: a cylindrical base portion 50 and a cuvette holder-positioner assembly 51. Base portion 50 is attached to the floor plate 64 of the instrument case or housing (not shown). Above the radiation apertures 13, 19, 21 and 23, the base 50 is provided with a vertically extending cylindrical hole 53 to receive a tightly fitted cylindrical base formed on the bottom end of cuvette holder-positioner 55.

Figure 4:
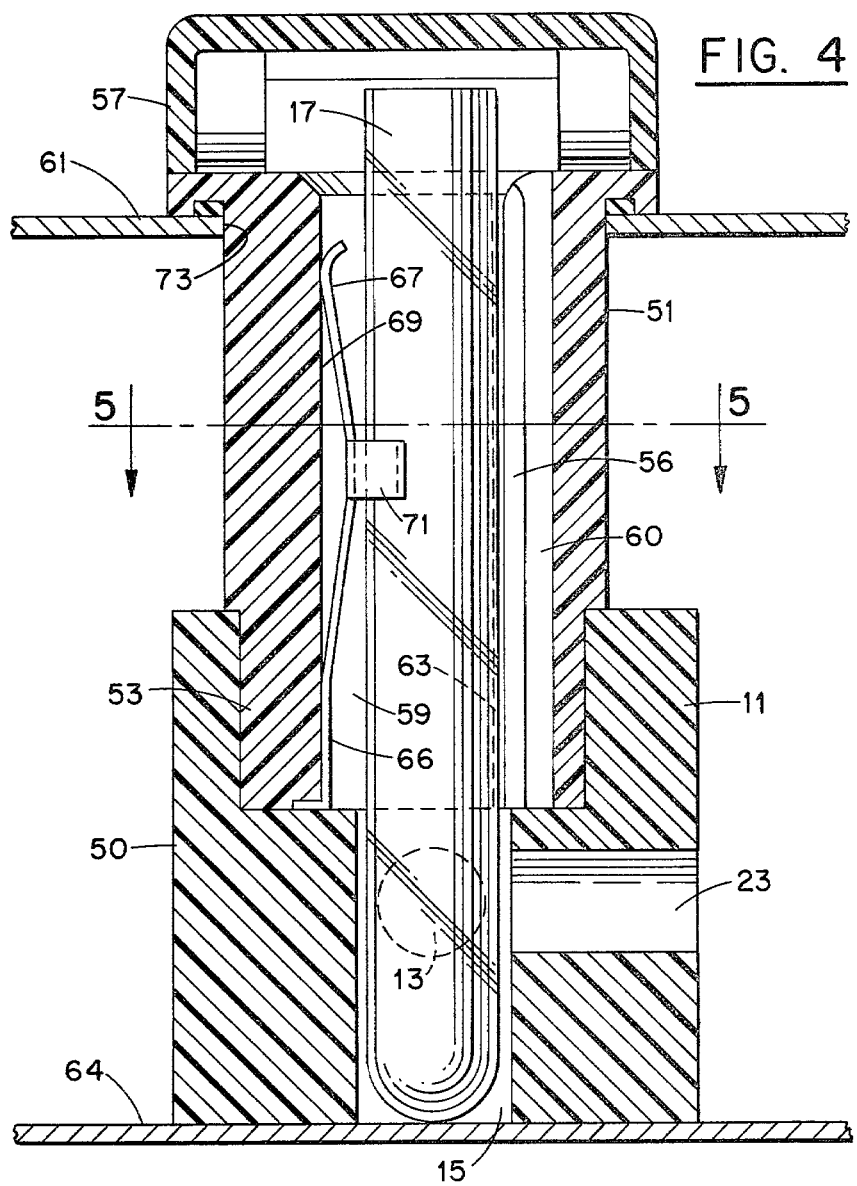
FIG. 4 shows a vertical sectional view of the plane taken along lines 4—4 of FIG. 3.
Figure 6:
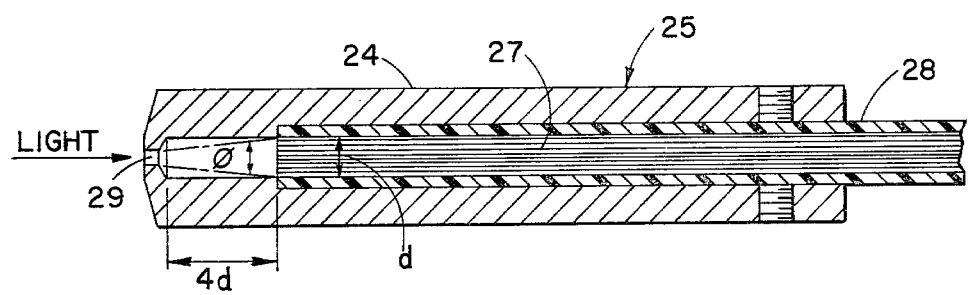
FIG. 6 shows an axial sectional view of the detector cone portion of the receptor-conveyor means.
Figure 5:
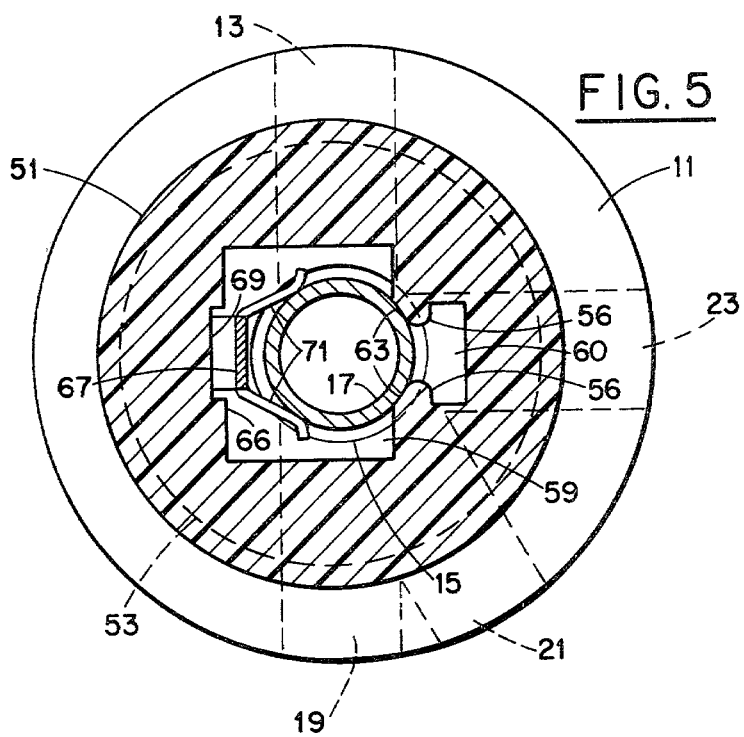
FIG. 5 shows a horizontal section view taken along lines 5—5 of FIG. 4.

A vertically extending rectangular hole 59 in-positioner 51 is in axial alignment with cylindrical hole 15 in base fixture 50 as is best seen in FIGS. 3, 4 and 5.

One wall of hole 59 has a rectangular axially extending recess 60; with flanges 56 extending partially into the opening between hole 59 and recess 60. The interior surface 63 of flanges 56 are inclined toward one another to form V-notch-positioning surfaces for a cuvette (best seen in FIG. 5).

On the rear wall 66 of hole 59, opposite flanges 56, is a leaf spring 67 secured in a groove 69. Spring 67 is bowed inwardly near its mid-point, as seen in FIG. 4, and at that location, there are two angularly extending fingers 71. Fingers 71 engage the cuvette and force it against surfaces 63, thus positioning the cuvette concentrically in hole 15 of base 50.

Cuvette holder-positioner 51 extends upwardly through an opening 73 in top plate 61 of the instrument housing, and a hinged lid 57 closes the hole 59 and covers cuvette 17.

The bottom end of cuvette 17 rests on floor plate 64 in the center of hole 15.

It will be apparent to those in the art that the cuvette fixture 11 as described will position all sample-holding cuvettes of the same standard size and shape accurately and identically in the path of the electromagnetic radiation.

In an apparatus according to the invention as shown in FIGS. 3-4, cuvette 17 rests on the floor plate 64 in the center of hole 15.

Sample-containing cuvettes are inserted into and removed from the apparatus by means of lid 57 (here Bausch & Lomb 33-31-27) being pivoted about hinge 58.

Attached to the cuvette fixture through one or more of the tubular radiation-receiving apertures are one or more receptor-conveyor means (receptor assemblies) for conducting the radiation transmitted through the cuvette and sample to one or more signal processing circuits according to the invention.

Referring to FIGS. 1, 3 and particularly 6, the receptor-conveyor means 25 (receptor assembly) comprises preferably a suitable flexible light transmission means, here a fiber-optic bundle 27. The fiber-optic bundle is terminated at one end (cuvette fixture end) by a substantially coaxial tubular detector cone 24, having an orifice 29 at the end of the detector cone opposite to the end of the fiber-optic bundle 27. The dimensions of the detector cone are such that the angle of admittance angle φ for radiation transmitted through orifice 29 to the fiber-optic bundle is from about about 5° to about 7°. The preferred admittance angle φ is about 6°, which is conveniently achieved by positioning the fiber-optic bundle at a distance of about four times (4d) the orifice diameter (d) from orifice 29. The detector cone 24 has the orifice 29 at the viewing or cuvette fixture end. The diameter of the orifice 29 is suitably machined so as to permit an optimum amount of light into the cone 24 to the bundle 27 without permitting diffracted light from the cuvette to reach the bundle 27. The diameter of the orifice 29 is constructed to allow the maximum light transmission through the contents of the cuvette without allowing the scattering of light to reach the bundle caused by any imperfections in the cuvette; generally, the diameter is preferably from about 0.35 to about 0.6 the diameter of the cone 24 (here about 0.037 inches is preferable), at the existing space relationships of the cone 24 from the cuvette 17 and the diameter of the cuvette 17. The fiber-optic bundle (diameter: here 0.093 inches not including the width of the ferrule) is inserted at the opposite end as noted (distance of about 4d). This cone eliminates the necessity of an optical lens assembly and azimuth mount used in the literature. The angle φ must not be so large as to entertain reflected light from the imperfect cuvettes often obtained in the field, but must not be so small as to block off light so as to require a specialized and unduly expensive light source. Detector cone 24, which is made of metal, such as brass, or other suitable material, is inserted by the user in a sealing engagement and locked with one of the radiation-receiving apertures. Fiber-optic bundle 27 is covered by a protective layer 28.

Figure 7:
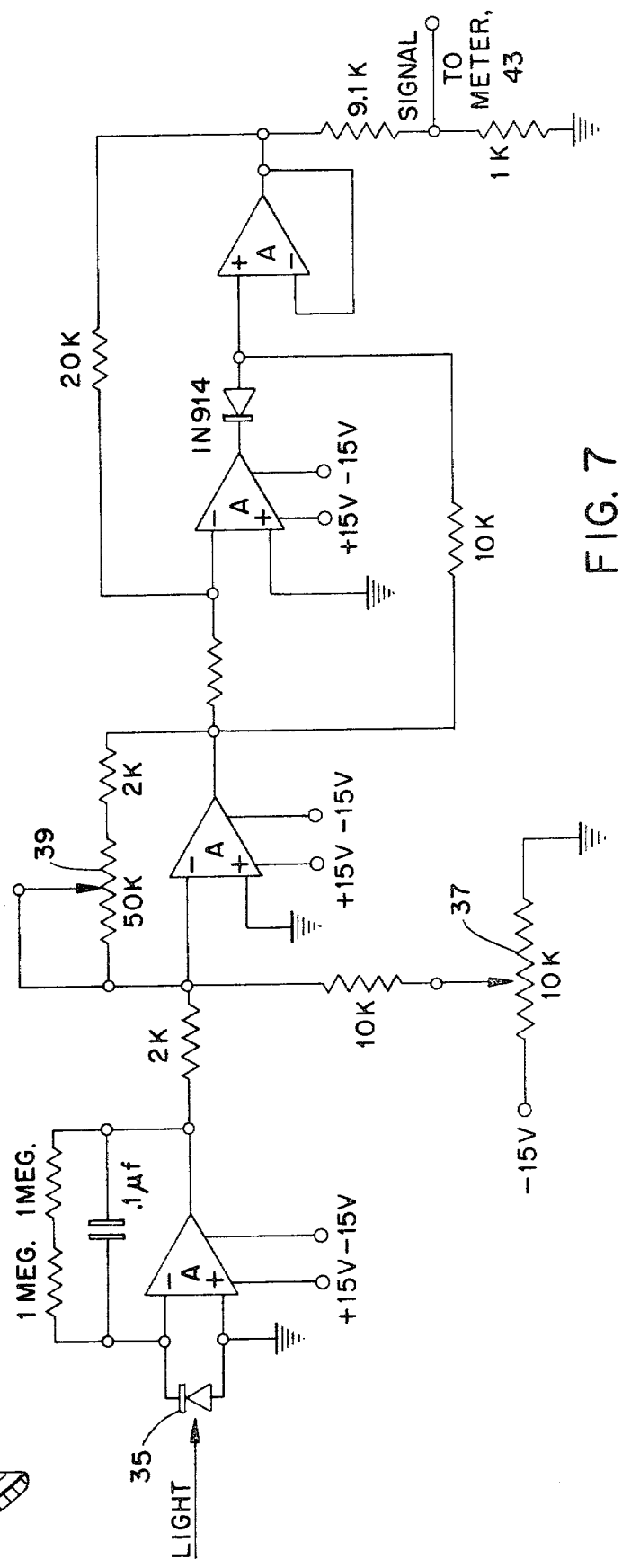
FIG. 7 represents a schematic diagram of the signal processing circuit.

The other end of fiber-optic bundle 27 is terminated at signal processing circuit 33. Referring to FIG. 7, showing a novel advanced signal processing circuit according to the invention, radiation that is transmitted from detector cone 24 through fiber-optic bundle 27 (not shown) impinges on a suitably-housed photodiode 35. Preferably, a silicon photodiode is employed (here UDT Pin 5D/SB). The radiation signal received by photodiode 35 is transferred, once the apparatus has been calibrated, using a sample containing a known quantity of an immunochemical substance as a standard, by means of the circuit shown, and particularly by means of a zero control subcircuit 37 (zero control by Helipot, 8136R50K) and a novel gain control subcircuit 39 (gain control by Helipot, 8136R50K), to an electrical signal transmitted to meter 43 (not shown). The circuit is especially useful in that it enables the photometric values measured by the invention to be amplified for detection readout. In general, the means (33 and 43 of FIG. 1) for detecting and measuring the transmitted beams comprises a photodiode-meter signal processing circuit including a means for amplifying a transmitted beam for a standard to a full-scale meter reading.

For measurement of HCG, infra, by a PREGNOSTICON ® Slide Test, any suitable circuit is functional that enables the operator to zero the instrument with a 0 IU HCG/l and then amplify the difference in transmitted or scattered light between the 0 IU HCG/l and 4500 IU HCG/l and display this value as a full scale reading.

Figure 8:
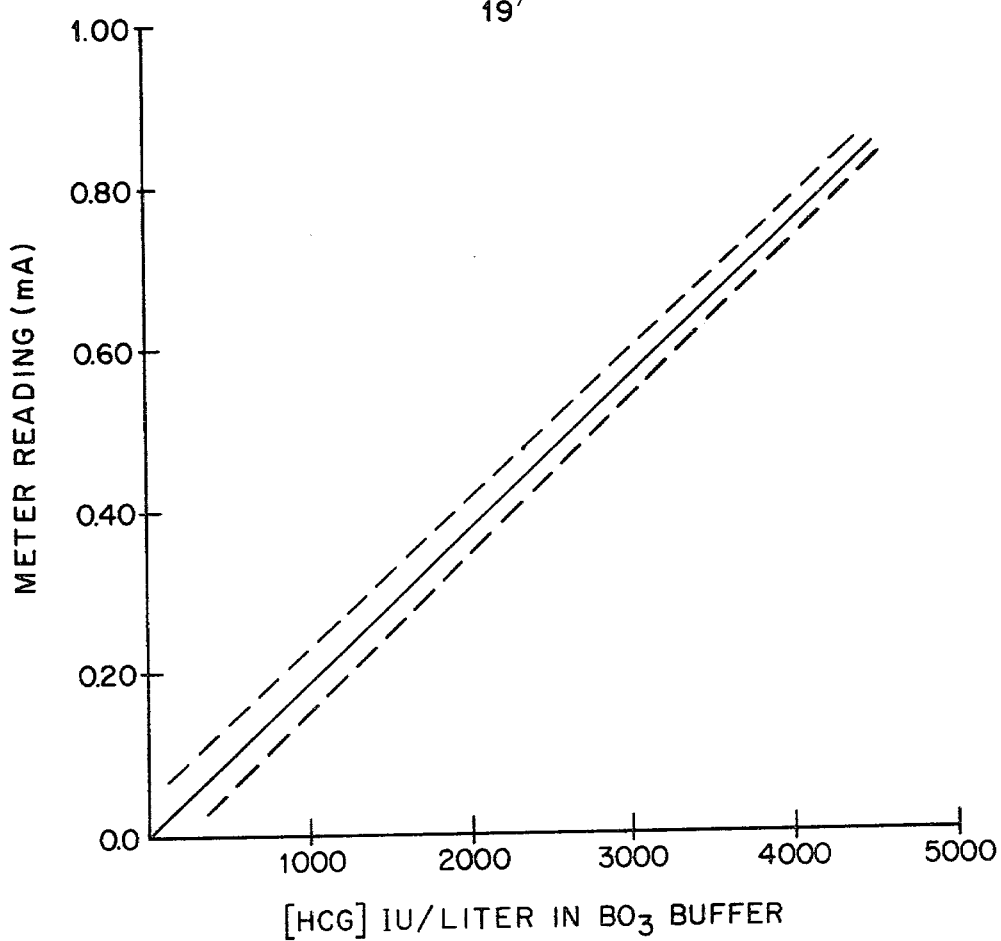
FIG. 8 is a graph illustrating the linear relationship between the concentration of the immunochemical substance and the meter reading, for use in Example III.

FIG. 8 (see Example III) is a graph illustrating a typical straight-line relationship between samples of known concentrations of an immunochemical substance and the corresponding meter readings. Therefore, using the method of the invention, the concentration of an immunochemical substance in a sample of unknown concentration can be determined directly from the meter reading.

The detector core portion of the receptor-conveyor means (receptor assembly) is engaged with a particular radiation-receiving aperture based on the particular electromagnetic radiation property that it is desired to measure. The preferred radiation-receiving aperture positions are at 0° for colorimetric determinations, 30° for scattered radiation determinations, and 90° for nephelometric determinations, such as, for example, wherein a fluorescent marker is employed (FIA), or for measuring total protein in urine, or for turbidimetry measurements, respectively.

The novel apparatus and method can also be used, for example, on fluorescent immunossays, providing that the 90° (or about 90°) radiation receiving aperture is used; and the fluorescent pigment has emission/excitation over 400 nm (example-fluorescein isocyanate, emission 492 nm, excitation 520 nm) which is larger than the mean diameter of the particles.

A method for detecting and measuring a predetermined specifically-bindable immunochemical substance according to the invention first comprises providing, in an immunoassay technique for a liquid sample, a component comprising a suspension of particles which may be agglutinated. Following the prescribed immunochemical reaction where agglutination may or may not have occurred, the electromagnetic radiation transmission properties of the sample are determined.

If the instrument is used for non-immunochemical purposes, such as for determining the clarity of liquids (for instance, wine), a filter after the light source need not be employed if the correct (suitable) electromagnetic radiation source is chosen corresponding to the designated purpose. It is well within the knowledge of those skilled in the photometric arts what radiation source should be selected for a particular purpose the instrument is to be employed for, how wide the wavelength range that must be provided by the radiation source, as well as the intensity that must be provided by the radiation source. Generally, one skilled in the art chooses for a particular purpose a radiation source having a sufficient wavelength range for the purpose intended, and if necessary, will employ a filter as, for example, that described above.

Although the invention has been described with respect to the specific embodiments above, numerous variations and modifications will become evident to those skilled in the art, without departing from the scope and spirit of the invention as described above, defined in the appended claims, and as shown in the following Examples:

EXAMPLE I

In one preferred embodiment of the invention, the immunochemical substance is detected and measured by measuring the electromagnetic radiation properties of a sample prepared using a "competitive" latex-agglutination method, here the PREGNOSTICON ® Slide Test kit by Organon Inc., West Orange, N.J.

Basically, according to the NOSTICON TM method, a liquid suspension of particles coated with an immunochemical substance having the same immunochemical properties as the immunochemical substance being detected and measured is prepared. The immunochemical substance used to coat the particles may be the identical immunochemical substance being detected and measured. In a preferred embodiment, the particles in suspension are latex particles.

In the PREGNOSTICON ® Slide Test, a latex agglutination inhibition test, a solution is prepared by mixing a suitable reagent (anti-HCG serum) such as shown below capable of specifically binding the immunochemical substance with a suitable liquid (urine) as shown below for which it is desired to detect and measure the immunochemical substance.

Then, the test solution is combined with the liquid suspension (latex). After allowing sufficient time for agglutination to occur, the electromagnetic radiation transmission properties are determined. The combined reagents, i.e, agglutination reaction, are suitably diluted with an appropriate buffer solution and mixed to facilitate the determination.

The PREGNOSTICON ® Slide Test is a special application of the above NOSTICON TM method and of an antigen-antibody reaction based on the principle of the Wide and Gemzell Pregnancy Test (*Acta Endocrenologica* 35, 1960), which is designed to demonstrate the presence of human chorionic gonadotropin (HCG) in urine. HCG is the antigen, and serum from rabbits immunized against HCG is the antibody.

According to the method here, polystyrene latex particles having a mean diameter of about 0.45 $\mu$m are washed in a 0.1 M borate buffer and then exposed to a pre-coating solution of bovine serum albumin. After further borate buffer washing, the latex particles are resuspended in a solution of human chorionic gonadotropin (HCG) and a period of sensitization follows.

The particles here in Example I were subsequently washed in borate buffer and placed in a final suspension fluid having a pH of 8.2. A dilution of rabbit anti-human chorionic gonadotropin serum was prepared so that in the presence of 1-2 IU HCG/ml (1000-2000 IU HCG/l) contained in a urine specimen, agglutination would be inhibited.

To perform these latex inhibition tests using the novel instrument, 0.05 ml of antiserum dilution was pipetted and mixed in a cuvette with 0.05 ml of urine specimen for a period of 30 seconds after which 0.05 ml of the latex suspension was added by pipette and the reaction mixture agitated for two minutes. For pipetting operations, a micropipettor is used, set for 50 $\mu$l delivery, with disposable tips. Ten milliliters (10.0 ml) of a 0.1 M borate buffer were added and the cuvette contents were mixed by inversion of the covered cuvettes two times. The reaction mixture was then placed in the cuvette fixture of the novel apparatus for readout of the amount of agglutination. Instead of a borate buffer, one may use a phosphate buffer, or a citrate buffer whose ionic strength does not exceed 0.3 M.

Figure 9:
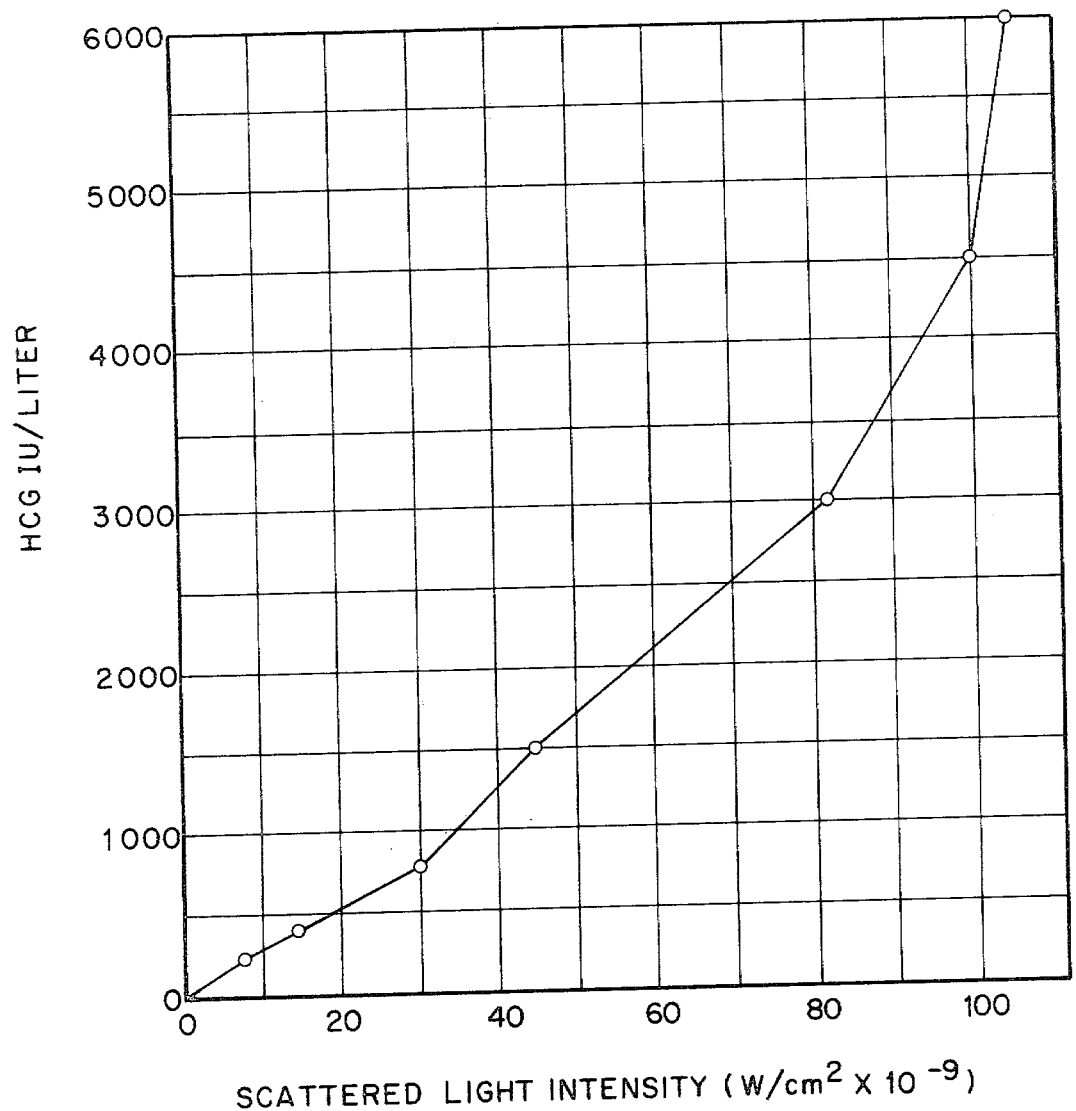
FIG. 9 is a graph illustrating the response of a preferred embodiment device to varying levels of HCG (see Example I).

In the case of inhibition of agglutination (a positive test for HCG) light transmission will be impeded by the homogeneous suspension; in a negative test, the latex and antiserum will form agglutinates leading to more light transmission through the contents of the cuvette. Bausch and Lomb Spectronic 20 ® cuvettes (or disposable 13 mm × 100 mm culture tubes) can be used for the novel apparatus of the invention. Tests were conducted using the PREGNOSTICON ® Slide Test Kit reagents above with different levels of HCG (IU/l) in borate buffer; the tests were read on the novel apparatus using a receptor-conveyor means (see 25 in FIG. 1) at an angle of 30° (i.e., means 25 placed in aperture 21) with respect to the extension of the axis of incident radiation beam aperture 13 of FIG. 1. As shown in FIG. 9, the data show an almost linear response by the instrument to varying levels of HCG (IU/l). Buffer dilution volumes less than ten milliliters (10.0 ml) may be used with similar success.

EXAMPLE II

A test using PREGNOSTICON ® Slide Test reagents was performed in the same manner as Example 1, however, actual urine samples, positive and negative for pregnancy were tested on the novel apparatus at 0°, 30°, and 90° to the extension of the axis of the incident radiation beam aperture 13 of FIG. 1. The data below clearly shows that at 0° and 30°, an average detectable difference of 20%–25% can be measured between the positive and negative clinical urine samples.

TABLE II

PREGNOSTICON ® SLIDE TEST CLINICAL TEST DATA

| SAMPLE | POSITIVE CLINICAL URINE ANGLE | | | MANUAL |
|---|---|---|---|---|
| | 0° | 30° | 90° | |
| 75 | 499 | 81.80 | 4.86 | + |
| 66 | 482 | 85.31 | 4.92 | + |
| 87 | 496 | 84.59 | 4.85 | + |
| 88 | 487 | 84.67 | 4.75 | + |
| NEGATIVE CLINICAL URINE | | | | |
| JK | 519 | 63.51 | 4.35 | − |
| MM | 521 | 61.96 | 4.24 | − |
| DS-2 | 537 | 60.81 | 4.29 | − |
| DS | 543 | 61.29 | 4.21 | − |
| MD | 502 | 67.47 | 4.12 | − |

Test Reacted in Tube
Test Diluted to 10 ml c̄ Borate Buffer
Readings @ 450 nm on Light-Scattering Test Stand
Readings are W/cm² × 10⁻⁸

EXAMPLE III

The purpose of this Example was to demonstrate the linear response of the novel instrument to varying levels of HCG (IU/l) in borate buffer. For this test or HCG calibration, the samples were prepared as exactly with Example I and II. The O HCG test was placed in the instrument and the zero control was adjusted for zero on the readout meter; the 4500 IU/l test placed in the instrument and the gain control was adjusted for a full-scale reading on the readout meter. Five known replicates of HCG dilutions from 0 to 4500 IU/l were tested on the novel instrument, as shown in FIG. 8. Linearity of the response of the novel apparatus to varying levels of HCG (IU/l) was demonstrated.

In the protocol, each sample was diluted with 10 ml of a 0.1 M borate solution as in Example I. All of the readings were at the 0° angle with a 450 nm filter, with five replicates taken of each HCG value. The equation $y = -1.38 + 0.002x$ was determined by a linear regression.

EXAMPLE IV

This example describes a modification of the GONOSTICON ® DRI-DOT ® latex agglutination test. Polystyrene latex particles having a mean diameter of 0.60 μm are washed in a 0.1 M borate buffer and then exposed to a pre-coating solution of bovine serum albumin. After further borate buffer washing, the latex particles are resuspended in a solution of gonococcal antigen (Gc9) and a period of sensitization follows. The particles are subsequently washed in 0.1 borate buffer and placed in a final suspension fluid.

To block or neutralize non-specific antibodies found in some human sera, an absorbing antigen prepared by combining the antigens of guinea pig extract and beef erythrocyte stroma is employed.

To perform the modified GONOSTICON ® DRI-DOT ® test using the novel apparatus of the invention, a 0.05 ml sample of human serum to be tested for the presence of gonococcal antibody is mixed in a cuvette with 0.05 ml of absorbing antigen. To this is added 0.05 ml of the GONOSTICON ® sensitized latex. The reaction mixture is agitated for two minutes, and 5.0 ml of 0.1 M borate buffer are added. The covered tube is then inverted twice for final mixing. The reaction mixture was then placed in the cuvette fixture of the novel apparatus for readout. The 0° position of the radiation receiving aperture was used.

If agglutination occurs due to the presence of antibody in the same and its combination with the latex antigen more light will be transmitted; in the absence of gonococcal antibody there will be no agglutination and the homogeneous suspension will impede light transmission through the contents of the cuvette.

EXAMPLE V

This example describes a modification of the RHEUMANOSTICON ® Slide latex agglutination test. Latex particles are prepared to receive a sensitizing coating of, in this instance, gamma globulin after being washed in a buffer solution, under the same conditions as above. After exposure of the latex to the gamma globulin for a period of time, the latex is washed to remove excess gamma globulin and taken up in a final suspension fluid having an alkaline pH (8.0–8.5).

To perform the modified RHEUMANOSTICON ® Slide test using the novel instrument of the invention, a 0.05 ml of serum sample suspected of having RF activity is mixed in a cuvette with 0.05 ml of RHEUMANOSTICON ® latex suspension. The reaction mixture is mixed by agitation after which 5.0 ml of glycine buffer of an effective concentration is added. The covered tube is then inverted twice for final mixing and the reaction mixture placed in the cuvette fixture of the novel apparatus. Again, the 0° position of the radiation receiving aperture was used.

If agglutination occurs due to the presence of RF in the sample and its combination with the latex antigen, more light will be transmitted; in the absence of RF there will be no agglutination, and the homogeneous suspension will impede light transmission through the contents of the tube.

EXAMPLE VI

In one embodiment the circuitry of FIG. 7 may be modified in order to present an easy to recognize display on the outside of the novel device a positive or negative result of the test. For example, in the PREGNOSTICON ® Slide Test protocol aforementioned in Examples I–III, the circuit can easily be modified to give a "amber light-green light" detection system. The use of this new circuit is as follows: a negative control sample test, i.e., O IU/liter HCG, is placed in the cuvette fixture; a zero-set button is pressed, automatically setting the instrument detection circuit to zero, and turning on the green light. Next, a borderline sample test, i.e., 1000 IU/liter HCG, is placed in the cuvette fixture and the green light will automatically turn on;

the gain control is adjusted until the panel meter reads 1000. The threshold control is adjusted until the green light turns off and the amber light turn on; the same control is backed off until the green light turns back on. In this mode any sample test of 1000 IU/liter HCG or less will turn on the green light; any sample test greater than 1000 IU/liter HCG will turn on the amber light; only one light will be on at any one time. Difficulties with the novel device operation of the "amber light-green light" system because of random temporary instabilities of the light transmission source (3 in FIG. 1—for example a quartz-halogen lamp) or line voltage perturbations have been corrected by modification of the circuitry of FIG. 7 to incorporate a standard 110 VAC voltage regulator.

Figure 10:
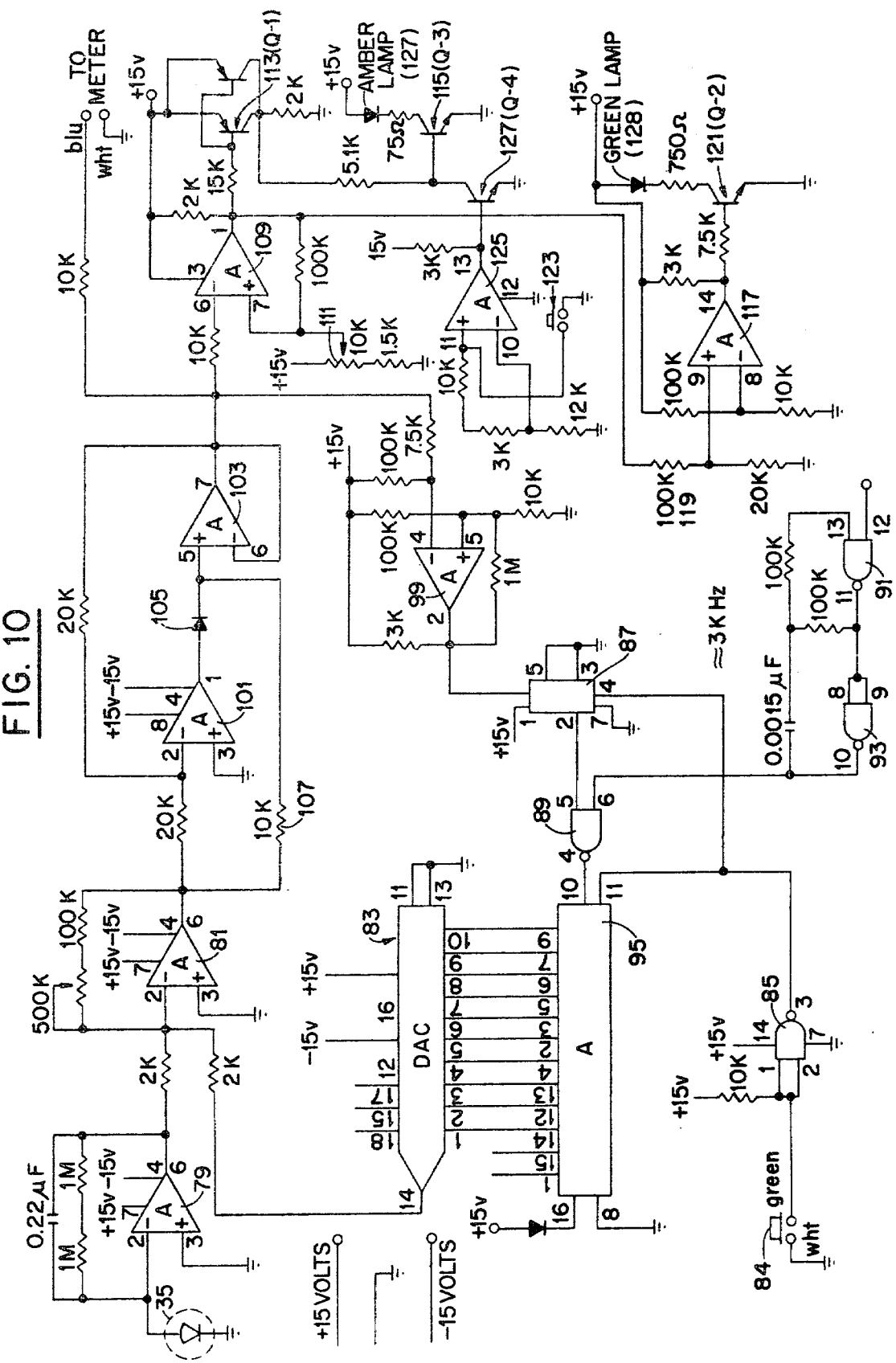
FIG. 10 represents a schematic diagram of a modification of the circuit of FIG. 7 (Example VI).

In FIG. 10 a signal processing and zero circuit is shown which not only encompasses much of FIG. 7 but is modified to give a "amber light-green light" indication for technical personnel. More specifically, when a light restricting object (such as a latex suspension of particles, turbidity sample, colored solution, etc.) is placed in the path of light striking the photodiode 35, the output current of the photodiode 35 is proportional to the amount of light striking it. This output current is amplified by a current to voltage amplifier 79. The output of amplifier 79 will be a negative voltage that is proportional to the current times the gain. This negative voltage is applied to a summing amplifier circuit 81, which is summed with an opposite polarity voltage from a digital to an analog circuit 83. This voltage from the digital to analog circuit 83 is the automatic zeroing voltage and is generated by pressing an auto zero button and releasing it.

When depressed and held in, an automatic zero button 84 grounds the input to nand gate 85. The output of gate 85 goes to a +15 volts, setting "flip-flop" amplifier 87 output to a +15 volts. This enables nand gate 89 to allow the clock pulse to pass through. The clock pulse is generated by amplifier 91 and amplifier 93 connected as a multivibrator, running at a frequency of approximately 3000 HZ. The output of amplifier 85 also drives digital counter 95. When gate 85 output is +15 volts, it sets digital counter 95, a 10 bit output, to zero. The 10 bit binary output drives digital to analog converter 83. The analog output from converter 83 will be zero volts when the 10 bit binary output digital counter 95 is at all zeros. When the automatic zero button 84 is now released, the output of gate 85 goes to zero volts, allowing digital counter 95 to start counting the clock pulses from gate 89 output. As binary number from counter 95 increases, the analog output from converter 83 increases accordingly. The analog output from converter 83 drives the summing amplifier 81. When the output from converter 83 is equal to the output of amplifier 79, and is the opposite polarity, the output of amplifier 81 will be zero volts; also the output of amplifier 103 will be zero volts. The comparator 99 detects the zero volts and its output switches to a +15 volts driving amplifier 87 (flip-flop) output to zero volts. This disables gate 89, stopping the clock pulses from driving digital counter 95. The binary output from digital counter 95 is now the stored digital value to drive the digital to analog converter 83. The circuit has now been automatically set at zero. The digital value for the zero sample that has been placed in the instrument is now stored in digital counter 95; the calibration meter will read zero and the green indicator lamp 128 will be on.

Successive readings for samples in the instrument will be with respect to the zeroing voltage driving the summing amplifier 81. The summing amplifier 81 has a gain control potentiometer 39 in its feedback circuit. If the light measuring object allows more light to pass with respect to the one used to zero the circuit, the output of amplifier 81 will be positive. The output of this summing amplifier 81 drives amplifier 101, an absolute value circuit. When the output of amplifier 81 is positive, the output of amplifier 101 is negative, reverse biasing a diode 105. This allows the positive signal to pass through resistor 107 into the non-inverting amplifier 103, resulting in a positive output. When the output of amplifier 81 is negative, the output of amplifier 101 is positive, forward biasing the diode 105. This allows the positive signal to pass through the diode into the non-inverting amplifier 103. The resulting output of amplifier 103 is always positive and drives a comparator circuit 109. This comparator circuit 109 compares the output from the amplifier 103 to the voltage that is set on the threshold control potentiometer 111. Whenever the output voltage of amplifier 103 is less positive than the positive voltage set on the potentiometer 111, the output of circuit 109 will be a positive 15 volts and represents a negative sample. When the output of amplifier 103 is more positive than the positive voltage set on the threshold potentiometer 111, the output of amplifier 109 will be zero volts and represents a positive sample.

When the output of amplifier 109 is at zero volts, the transistor 113 is turned on, causing transistor 115 to conduct and to light the amber light emitting diode indicator 127, indicating a positive sample. When the output of amplifier 109 is at a +15 volts, transistors 113 and 115 are in a non-conducting condition and the positive indicator is off. The +15 volts from amplifier 109 drives a comparator circuit amplifier 117, through resistor 119. Whenever the input to resistor 119 is a +15 volts, the output of amplifier 117 is a +15 volts causing transistor 121 to conduct, turning on the green light emitting diode indicator 128 for a negative sample. The switch 123 is a normally-open switch located at the base of the cuvette detection fixture.

When a cuvette is not in the detection fixture, switch 123 is open and the output of comparator 125 is +15 volts, causing transistor 127 to conduct. When transistor 127 is in a conducting mode, both LED circuits are disabled. When a cuvette is fully inserted into the detection fixture, switch 123 is depressed and held closed, driving comparator 125 to zero volts. This drives transistor 127 into a nonconducting mode, thus permitting the LED circuits to function according to the amount of light passed through the cuvette samples of the threshold control potentiometer 111 voltage setting.

The following parts represent the preferred devices for key components in FIG. 10:

| | |
|---|---|
| 79, 81 | AD-741 by Analog Devices, Inc. |
| 103, 101 | MC-1458 by Motorola |
| 99, 109, 117, 125 | LM-339 by Analog Devices, Inc. |
| 87 | MC-14013 CP by Motorola |
| 85, 93, 91, 89 | MC-14011 CP by Motorola |
| 95 | MC-14040 CP by Motorola |
| 83 | DAC-03-DOX1 by Precision Monolithic, Inc. |

A sample test tube placed in the instrument activates switch 123 to a closed condition. The output of amplifier 125 goes to zero volts which drives transistor 127 into a non-conducting condition enabling the light emitting diode indicators to function.

As one skilled in the art can now appreciate, the novel features of the invention may have many applications in photometry (for studying molecular and micellar weights of compounds, particle size and size distribution shapes of macromolecules, interactions in solutions, etc., as mentioned above); hence, in its broadest aspect the novel photometer may be used for any purpose related to detecting and measuring electromagnetic radiation at predetermined angles through a liquid sample, and comprises:

(a) a suitable electromagnetic radiation source capable of providing radiation over a predetermined wavelength range;

(b) means for concentrating and collimating radiation from said electromagnetic radiation source to form a beam;

(c) means for (i) positioning a sample-containing cuvette in the path of the beam and for (ii) allowing the beam incident on the cuvette to be transmitted through the cuvette and sample, and for (iii) receiving a portion of the beam transmitted through the sample at two or more predetermined angles with respect to the beam, comprising:

a cuvette fixture comprising a tubular incident radiation beam aperture, a tubular cuvette opening, and at least two tubular radiation-receiving apertures, wherein the axes of all the apertures are coplanar and intersect along the axis of the cuvette opening and are perpendicular to the cuvette opening, and wherein the axes of the radiation-receiving apertures are fixed at predetermined angles with respect to the axes of (1) the incident radiation beam aperture and (2) the tubular cuvette opening, and attached thereto; and a receptor-conveyor means comprising a tubular fiber-optic bundle terminated at one end by a substantially coaxial tubular detector cone, wherein the detector cone is (1) inserted in sealing engagement with one of said radiation-beam receiving apertures, and (2) has a substantially coaxial orifice at the end of the detector cone remote from the bundle, with dimensions such that electromagnetic radiation is transmitted at about a 6° admittance angle from the orifice to said fiber-optic bundle, and being at the intersection of the receiving aperture and the cuvette opening; and (e) means with the non-terminated end of the fiber-optic bundle and with the cuvette-positioning means for detecting and measuring substantially only a portion of the transmitted beam.

What is claimed is:

1. An apparatus for detecting and measuring electromagnetic radiation transmitted at predetermined angles through a liquid sample having a suspension of particles, said apparatus comprising:

(a) a suitable electromagnetic radiation source capable of providing radiation at wavelengths equal to or less than the mean diameter of the particles;

(b) means for concentrating and collimating radiation from said electromagnetic radiation source to form a beam;

(c) means for filtering the beam to (i) eliminate radiation having wavelengths greater than the mean diameter of the particles and (ii) transmit radiation at a wavelength below the mean diameter of the particles over a wavelength range of at least 100 nm;

(d) means for (i) positioning a sample-containing cuvette and for (ii) allowing the filtered beam incident on the cuvette to be transmitted through the cuvette and sample, and for (iii) receiving a portion of the filtered beam transmitted through the sample at two or more predetermined angles with respect to the beam, comprising:

a cuvette fixture comprising a tubular incident radiation beam aperture, a tubular cuvette opening, and at least two tubular radiation-receiving apertures, wherein the axes of all the apertures are coplanar and intersect along the axis of the cuvette opening and are perpendicular to the cuvette opening, and wherein the axes of the radiation-receiving apertures are fixed at predetermined angles with respect to the axes of (1) the incident radiation beam aperture and (2) the tubular cuvette opening, and attached thereto; and a receptor-conveyor means comprising a tubular fiber-optic bundle terminated at one end by a substantially coaxial tubular detector cone, wherein the detector cone is (1) inserted in sealing engagement with one of said radiation-beam receiving apertures, and (2) has a substantially coaxial orifice at the end of the detector cone remote from the bundle at a distance such that electromagnetic radiation is transmitted at about a 6° admittance angle from the orifice to said fiber-optic bundle, said orifice being at the intersection of the receiving aperture and the cuvette opening; and (e) means with the non-cone-terminated end of the fiber-optic bundle and with the cuvette-positioning means for detecting and measuring substantially only a portion of the transmitted beam.

2. An apparatus as in claim 1 wherein the electromagnetic radiation source is capable of providing radiation over a wavelength the range of at least 100 mn below about 450 nm.

3. An apparatus as in claim 2 wherein the electromagnetic radiation source is a quartz-halogen lamp.

4. An apparatus as in claim 2 wherein the means for filtering the beam to eliminate radiation having wavelengths longer than the mean diameter of the particles while transmitting radiation below 450 nm over a range of at least 100 nm is a low-pass optical filter.

5. An apparatus as in claim 2 wherein the low-pass optical filter transmits radiation in the range of about 300 nm to about 450 nm.

6. An apparatus as in claim 2 wherein the means for detecting and measuring a portion of the transmitted beam comprises a photodiode-meter signal processing circuit including a means for amplifying a transmitted beam for a standard to a full-scale meter reading.

7. A photometer for detecting and measuring electromagnetic radiation transmitted at predetermined angles through a liquid sample, comprising:

(a) a suitable electromagnetic radiation source capable of providing radiation over a predetermined wavelength range;

(b) means for concentrating and collimating radiation from said electromagnetic radiation source to form a beam;

(c) means for (i) positioning a sample-containing cuvette in the path of the beam and for (ii) allowing the beam incident on the cuvette to be transmitted through the cuvette and sample, and for (iii) receiving a portion of the beam transmitted through the sample at two or more predetermined angles with respect to the beam, comprising:

a cuvette fixture comprising a tubular incident radiation beam aperture, a tubular cuvette opening, and at least two tubular radiation-receiving apertures, wherein the axes of all the apertures are coplanar and intersect along the axis of the cuvette opening and are perpendicular to the cuvette opening, and wherein the axes of the radiation-receiving apertures are fixed at predetermined angles with respect to the axes of (1) the incident radiation beam aperture and (2) the tubular cuvette opening, and attached thereto; and a receptor-conveyor means comprising a tubular fiber-optic bundle terminated at one end by a substantially coaxial tubular detector cone, wherein the detector cone is (1) inserted in sealing engagement with one of said radiation-beam receiving apertures, and (2) has a substantially coaxial orifice at the end of the detector cone remote from the bundle, with dimensions such that electromagnetic radiation is transmitted at about a 6° admittance angle from the orifice to said fiber-optic bundle, and being at the intersection of the receiving aperture and the cuvette opening; and (e) means with the non-terminated end of the fiber-optic bundle and with the cuvette-positioning means for detecting and measuring substantially only a portion of the transmitted beam.

* * * * *

UNITED STATES PATENT OFFICE
CERTIFICATE OF CORRECTION

Patent No. 4,250,394     Dated February 10, 1981

Inventor(s) John J. O'Connor

It is certified that error appears in the above-identified patent and that said Letters Patent are hereby corrected as shown below:

On the front page of the patent (disclosing the inventor, assignee, Abstract, etc.), under "References Cited, U.S. Patents", add the following references:

| | | |
|---|---|---|
| 4,157,871 | Anderson | 23/230BX |
| 3,824,402 | Mullaney | 250/574 X |
| 3,905,767 | Morris et al | 250/574 X |
| 3,967,901 | Rodriquez | 250/574 X |
| 4,118,192 | Sawaii et al | 422/56 X |
| 4,204,837 | Sternberg et al | 23/230 B |

On the same front page, under "References Cited--Other Publications", add

"Automated Analysis Part 2", Robert F. Ritchie, pp.442-48, Marcel Dekker & Co., N.Y. 1978".

"Laser Fluorescence Immunoassays with beta-Galactosidase Enzyme Label Can Help Measure Insulin Levels in Human Blood Serum", C & E News, March 31, 1980, p. 5.

Chemical Week, April 2, 1980, at 42 (Abstract).

In Col. 2, line 46, underline 39, and insert a "," before "1157".

In Col. 6, line 35, insert ")" after "FIA".

In Col. 9, line 32, correct the spelling of "Acta".

UNITED STATES PATENT OFFICE
CERTIFICATE OF CORRECTION

Patent No. 4,250,394　　　　　Dated February 10, 1981

Inventor(s) John J. O'Connor

It is certified that error appears in the above-identified patent and that said Letters Patent are hereby corrected as shown below:

In Col. 15, line 56, "33-31-27" should not be in bold print.

In Col. 18, line 63, "20" should not be in bold print.

In Col. 19, line 69, "9" in "Gc9" should not be in bold print.

In Col. 20, line 63, change letter "O" to number "0".

Signed and Sealed this

Eleventh Day of August 1981

[SEAL]

Attest:

GERALD J. MOSSINGHOFF

Attesting Officer　　Commissioner of Patents and Trademarks